United States Patent [19]

Jiang et al.

[11] Patent Number: 5,961,889
[45] Date of Patent: Oct. 5, 1999

[54] PROCESS OF PRODUCING POLYTHIOL OLIGOMER

[75] Inventors: Jian Jiang; Masahisa Kosaka, both of Akiruno, Japan

[73] Assignee: Hoya Corporation, Tokyo, Japan

[21] Appl. No.: 08/845,407

[22] Filed: Apr. 25, 1997

[30] Foreign Application Priority Data

Apr. 26, 1996 [JP] Japan .................................. 8-108032
Aug. 28, 1996 [JP] Japan .................................. 8-226736

[51] Int. Cl.$^6$ .................................................. C08G 75/00
[52] U.S. Cl. ........................ 252/582; 252/587; 252/589; 528/85; 528/377
[58] Field of Search .................... 252/582, 587, 252/589; 528/85, 377

[56] References Cited

U.S. PATENT DOCUMENTS

| | | | |
|---|---|---|---|
| 2,237,625 | 4/1941 | Olin ........................................ | 252/582 |
| 3,219,638 | 11/1965 | Warner .................................... | 528/377 |
| 5,326,501 | 7/1994 | Ohkubo et al. .......................... | 252/582 |
| 5,403,938 | 4/1995 | Ohkubo et al. ............................ | 549/22 |
| 5,464,931 | 11/1995 | Shaw et al. ............................. | 524/714 |
| 5,565,517 | 10/1996 | Efner et al. ............................. | 524/714 |

FOREIGN PATENT DOCUMENTS

| | | |
|---|---|---|
| 0 562 966 | 9/1993 | European Pat. Off. . |
| 7-118263 | 5/1995 | Japan . |
| 7-118390 | 5/1995 | Japan . |

OTHER PUBLICATIONS

B. D. Vineyard, "The Versatility and the Mechanism of the n–Butylamine–Catalyzed Reaction of Thiols with Sulfur", Dec. 1967, J. Org. Chem., vol. 32, 3833–3836.

Journal of Applied Polymer Science, vol. 23, No. 9, pp. 2757–2761, "Kinetic of the Base–Catalyzed Reactions of Cyclooctameric Sulfur with Dithiol", B. K. Bordoloi et al, XP002042192.

Journal of Organic Chemistry, vol. 32, Dec. 1967, pp. 3833–3836, XP002042193, "The Versatility and the Mechanism of the N–Butylamine–Catal. Reaction of Thiols with Sulfur", B. D. Vineyard.

Chemical Abstracts, vol. 123, No. 35, 1995, Abstract No. 113212x, p. 33, col. 2, XP002042194, and JP 07 117 263 A (Hoya).

*Primary Examiner*—Terressa Mosley
*Attorney, Agent, or Firm*—Griffin, Butler Whisenhunt & Szipl, LLP

[57] ABSTRACT

A process for producing a polythiol oligomer having disulfide linkages by reacting polythiol (with the functionality of two or above) with sulfur in a molar ratio of m to (m−1) (where m is an integer of 2 to 21) in the presence of a basic catalyst, whereby the oligomers produced have a degree of oligomerization of m (wherein m is defined as above). Specifically disclosed is a process for reacting 2,5-dimercaptomethyl-1,4-dithiane (DMMD) with sulfur in a molar ratio 2:1 or 3:2 in the presence of a basic catalyst, thereby producing an oligomer represented by the below formula:

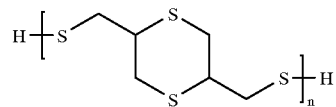

(wherein n is an integer of up to 21). Also disclosed are optical polymers made with the oligomer and optical materials and devices made with the polymer.

27 Claims, 2 Drawing Sheets

PROCESS OF PRODUCING POLYTHIOL OLIGOMER

BACKGROUND OF THE INVENTION

1. Field of the Invention

The present invention relates to a process for producing a polythiol oligomer with disulfide linkages in its backbone, which is useful as a raw material for optical polymer materials and devices. The process of the present invention affords a polythiol oligomer with a high refractive index and a high Abbe's number (or a low dispersive power). Therefore, the polythiol oligomer is suitable as a raw material to produce an optical polymer with good optical properties such as a high refractive index and a high Abbe's number (or a low dispersive power). The invention further relates to an optical polymer made from said polythiol oligomer and useful for the production of optical materials and devices. Polymers made from the above oligomers find wide application in, for example, optical lenses, eyeglass lenses, contact lenses, intraocular lenses, prisms, optical filters, optical fibers, optical disk substrates, etc.

2. Description of the Related Art

Plastics have recently come into common use in optical devices such as lenses because of their advantages over glass, in, for example, weight, crack resistance, and dyeability. Examples of optical plastics now in practical use include poly(diethylene glycol bisallyl carbonate), polymethyl methacrylate, and polycarbonate.

Glass and plastics used as optical materials generally decrease in Abbe's number as the refractive index increases, and vice versa. This means that it is generally very difficult to produce a plastic optical material having both a high Abbe's number and a high refractive index.

This difficulty has been overcome to some extent by a new plastic lens disclosed in Japanese Patent Laid-open No. 236386/1991. The reference relates to a polythiourethane lens obtained by reaction between a polythiol and a polyisocyanate. The disclosed polythiol is derived from 2,5-dimercaptomethyl-1,4-dithiane (referred to as DMMD hereinafter). Since DMMD has a high refractive index of 1.646 and a high Abbe's number of 35.2, the polythiourethane lens obtained from the polymerization of this monomer also has a high refractive index and a high Abbe's number. Despite these developments, there is still a strong demand for the development of new plastic lenses having higher refractive indexes and higher Abbe's numbers.

To meet this demand, Japanese Patent Laid-open Nos. 118263/1995 and 118390/1995 propose a process for producing another polythiourethane lens. The disclosed process includes oxidizing DMMD with air in the presence of a catalyst (such as methylsulfoxide and ferric chloride), thereby giving a mixture of DMMD oligomers, and reacting this mixture with polyisocyanate.

Unfortunately, the oligomers obtained by this process fluctuate in refractive index from 1.665 to 1.680 and in Abbe's number from 34.3 to 35.0, when reaction conditions such as temperature and humidity are slightly changed. Thus, the properties of the oligomer are unstable and an oligomer mixture having fixed, predictable properties is difficult to obtain. Consequently, it is difficult to form an optical polymer or material having a fixed refractive index and fixed Abbe's number. Therefore, the disclosed mixture of DMMD oligomers is of limited use for optical materials.

U.S. Pat. No. 2,237,625 discloses a process for producing a mixture of disulfide, trisulfide, and tetrasulfide by reaction between alkylmercaptan (monothiol) and sulfur in equimolar amounts in the presence of amine catalyst. B. D. Vinejard reported the same reaction as above catalyzed by n-butylamine, in Journal of Organic Chemistry, No. 32, p. 3833, 1967. However, these disclosed reactions are neither intended to synthesize polythiol oligomers from a polythiol with the functionality of two or above, nor to be used to produce optical polymer raw materials.

SUMMARY OF THE INVENTION

It is an object of the present invention to provide a process for selectively producing a stable polythiol oligomer comprising in large part dimers and trimers with a functionality of two or more. It is a further object to produce such an polythiol oligomer having a higher refractive index than and an Abbe's number comparable to the starting polythiol.

In order to achieve the above-mentioned objects, the present inventors have carried out research to determine whether it is possible to selectively produce in a stable manner a polythio oligomer composed mainly of m monomeric units of polythiol by reaction between polythiol (with the functionality of two and above) and sulfur in a molar ratio of m to (m−1) (where m is an integer of 2 to 21) in the presence of a basic catalyst.

It is a further object of the present invention to provide a practical optical polymer suitable for making optical materials and devices, and to provide an optical polymer that has a stable high refractive index and a stable high Abbe's number (low optical dispersion) by using the oligomer produced according to the present invention.

In accordance with the above objects the inventors have provided a process for producing a polythiol oligomer having disulfide linkages, comprising reacting polythiol (with the functionality of two or above) with sulfur in a molar ratio of m to (m−1) (where m is an integer of 2 to 21) in the presence of a basic catalyst, whereby the oligomers produced have a degree of oligomerization of m (wherein m is defined as above).

More particularly, the present invention relates to a process for reacting 2,5-dimercaptomethyl-1,4-dithiane (DMMD) with sulfur in a molar ratio 2:1 or 3:2 in the presence of a basic catalyst, thereby producing an oligomer represented by the below formula:

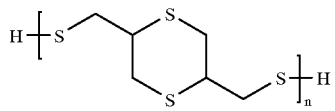

(wherein n is an integer of up to 21)

In a further embodiment, the invention provides a practical optical polymer suitable for making optical materials and devices, and having a stable high refractive index and a stable high Abbe's number (low dispersion) by using a specific oligomer having a stable high refractive index and a stable high Abbe's number (low dispersion) as a polythiol group-containing component and copolymerizing the same with a polyisocyanate group-containing component and/or a polyfunctional vinyl group-containing component.

In yet another embodiment, the present invention provides an optical polymer formned by copolymerizing a monomer mixture comprising:

(A) a polythiol group-containing component,
(B) a polyisocyanate group-containing component and/or
(C) a polyfunctional vinyl group-containing component.

The polymer thus produced provides optical characteristics appropriate for use as an optical material having a stable high refractive index and a stable high Abbe's number (low dispersion). Component A includes the oligomer represented by formula (I)

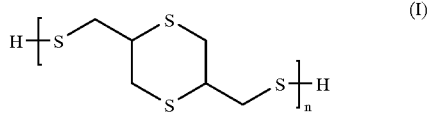

(wherein n is an integer of up to 21), produced by the process of the present invention.

In a still further embodiment of the present invention, component A comprises the polythiol ologomer a1 of the present invention, a disulfide-bond-free polythiol component a2, and/or a disulfide-bond-containing polythiol oligomer component a3.

Further objects, features and advantages of the present invention will become apparent from the Description of the Preferred Embodiments which follows, when considered together with the attached drawings.

DESCRIPTION OF THE PREFERRED EMBODIMENTS

Figure 1:
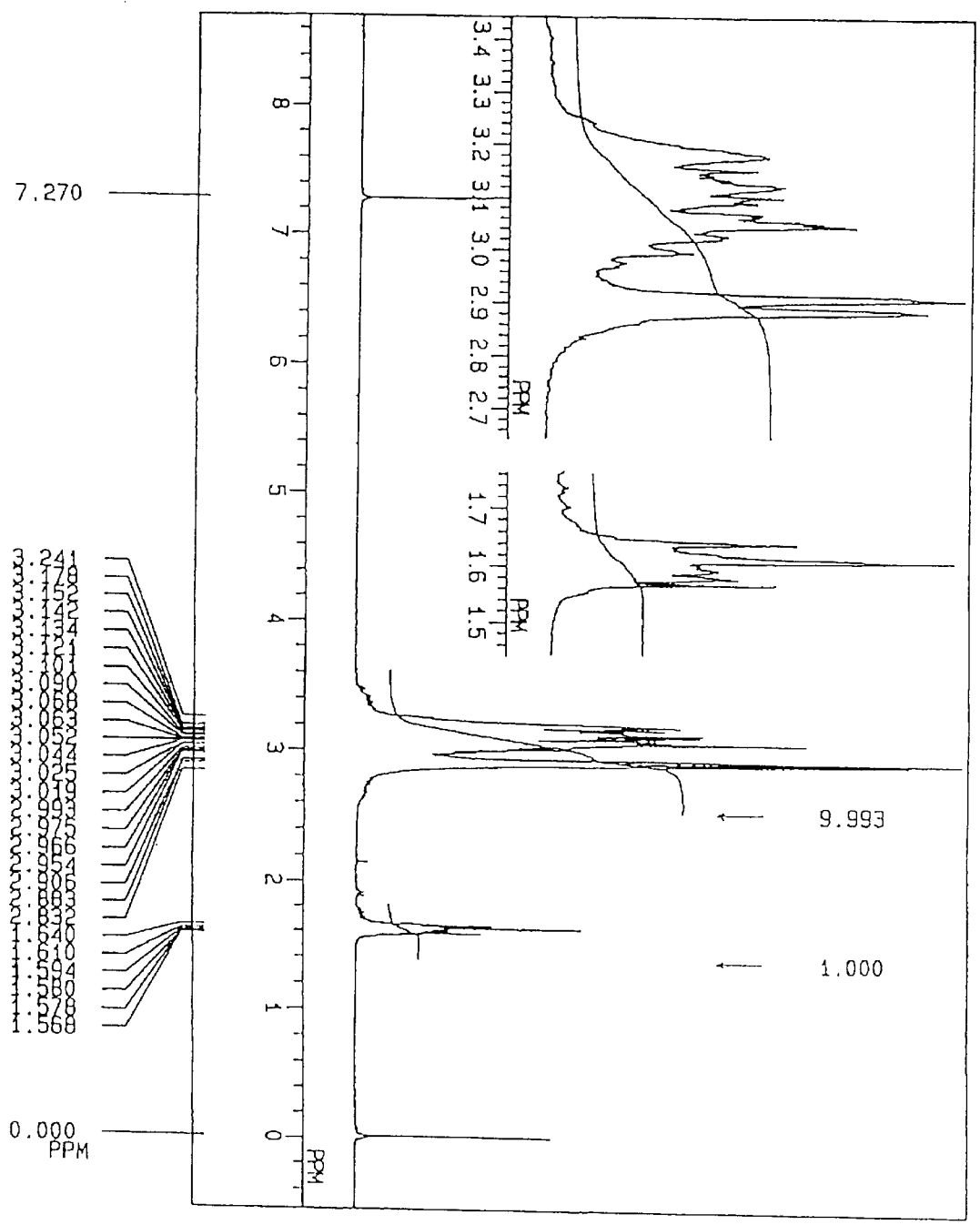
FIG. 1 is a $^1$H-NMR spectrum of the oligomer produced in Example 1.

The embodiments of the present invention will be described in detail as follows.

1. Polythiol Oligomer of the Invention

According to the process of the present invention, the synthesis of an oligomer of polythiol is represented by the following reaction formula.

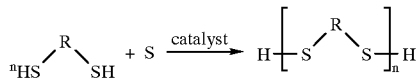

(wherein R stands for any organic moieties with 1 or 2 of hydroxy or/and thiol groups and n is any integer over 1.)

Although the synthesis of an oligomer composed in large part of dimers from 2 mol of thiol and 1 mol of sulfur is shown above, the same process can be used for the synthesis of an oligomer composed in large part of m monomeric units (m is 3 or above) except that the molar ratio of polythiol to sulfur is changed to m to (m−1). In other words, the molar ratio is 3:2 for the synthesis of an oligomer composed in large part of trimers (m=3) and the molar ratio is 4:3 for the synthesis of an oligomer composed mainly of tetramers (m=4).

The process of the present invention employs polythiol with the functionally of two or above, which may be linear, branched, or cyclic. The polythiol may have other functional groups such as amino group and hydroxyl group so long as it has two or more mercaptan groups. Examples of the polythiol of the present invention include 2,5-dimercaptomethyl-1,4-dithiane (DMMD), pentaerythritol tetramercaptoacetate, pentaerythritol tetramercaptopropionate, trimethylolpropane trimercaptoacetate, 2,3-dimercapto-1-propanol, 2-mercaptoethylsulfide, 2,3-(dimercaptoethylthio)-1-mercaptopropane, 1,2,3-trimercaptopropane, ethanedithiol, butanedithiol, hexanedithiol, benzenedithiol, toluenedithiol, and xylylenedithiol. Of these examples, DMMD is especially useful for the production of polythiol having a high refractive index and a high Abbe's number (ie., a low dispersive power).

The process of the present invention may use sulfur in any form, such as crystalline, colloidal, powder, and sublimed sulfur. The purity of the sulfur should be higher than 98%, preferably higher than 99%.

The process of the present invention employs a basic catalyst which should preferably be ammonia or amine. The amine may be linear, branched, alicyclic, or aromatic. It may also be primary, secondary, or tertiary. Examples of the catalyst include ammonia, ethylamine, diethylamine, triethylamine, n-propylamine, isopropylamine, n-butylamine, s-butylamine, t-butylamine, n-amylamine, morpholine, piperidine, substituted morpholine, substituted piperidine, and aniline. Preferable are diethylamine, triethylamine, n-butylamine, and morpholine. The amount of the catalyst (ammonia or amine) is usually 0.001–1.0 mol %, preferably 0.01–0.1 mol %, based on the polythiol starting material. The catalyst may be mixed with polythiol and sulfur before the resulting mixture is charged into the reaction system, or may be added to the reaction system after polythiol and sulfur have been mixed together and the sulfur has been completely dissolved.

The process of the present invention may employ a solvent. Examples of suitable solvents include halogenated hydrocarbons (such as dichloromethane, chloroform, carbon tetrachloride, dichloromethane, dichloroethane, and trichloroethane), aliphatic hydrocarbons (such as hexane and the like), alicyclic hydrocarbons (such as cyclohexane and the like), aromatic hydrocarbons (such as benzene, toluene and the like), alcohols (such as methanol, ethanol, isopropanol, and the like), and ethers (such as dimethyl ether, diethyl ether, tetrahydrofuran and the like). The amount of solvent varies depending on the starting material, the catalyst, and the conditions of synthesis.

The process of producing an oligomer according to the present invention is not specifically restricted in reaction temperature. It may be carried out at temperatures in the range from room temperature to the boiling point of solvent, preferably in the range of room temperature to 120° C.

EXAMPLES

The invention will be described in more detail with reference to the following examples, which should not be construed as restricting the scope of the invention.

Physical properties in the examples were measured according to the following methods.

$^1$H-NMR: determined with JEOL EX-270 NMR spectrometer

IR: determined with FT300 infrared spectrometer

Refractive index ($N_d$) and Abbe's number ($V_d$): measured with a Kalnew Automatic Digital Precision Refractometer (KPR-200)

Measurements were carried out at 25° C. unless otherwise specified.

Appearance: by visual inspection

Example 1

A 500 ml round-bottomed flask was charged with 84.8 g (0.4 mol) of 2,5-dimercaptomethyl-1,4-dithiane (DMMD), 6.4 g (0.2 mol) of sulfur powder, 0.014 g (0.05 mol % for DMMD) of diethylamine as the catalyst, and 95 ml of tetrahydrofuran (THF) as the solvent. The molar ratio of DMMD/S in this example was 2/1. The reactants were heated with stirring in an oil bath at 60° C. The reaction began to proceed, with the liquid surface taking on a brown color, along with the dissolution of sulfur. The reaction continued for about 20 minutes, with hydrogen sulfide being evolved vigorously in large quantities. After about 30 minutes, hydrogen sulfide was no longer evolved. The bath temperature was raised to 100° C., and THF was distilled away. After THF had been mostly distilled away, THF was removed completely by passing nitrogen gas through the reactant reaction system for 2 additional hours. Thereafter the reaction product was deaerated under vacuum at 100° C. A polythiol oligomer was thus obtained composed mainly of (4-mercaptomethyl-2,5-dithianyl)methyldisulfide in the form of colorless, transparent viscous liquid. The yield was about 100%. The oligomer was found to be in large part dimers and trimers of DMMD, with monomers and higher oligomers also present. This oligomer was found to have a refractive index of 1.682 and an Abbe's number of 34.7. In addition, it had the following NMR data and IR data:

$^1$H-NMR (solvent: CDCl$_3$, internal standard: TMS)
 d (ppm): 1.61 (t 1.0 H), 2.83–3.24 (m 10.0 H)
IR: 2550 cm$^{-1}$ (n for thiol SH),
 550 cm$^{-1}$ (n for disulfide SS)

Figure 2:
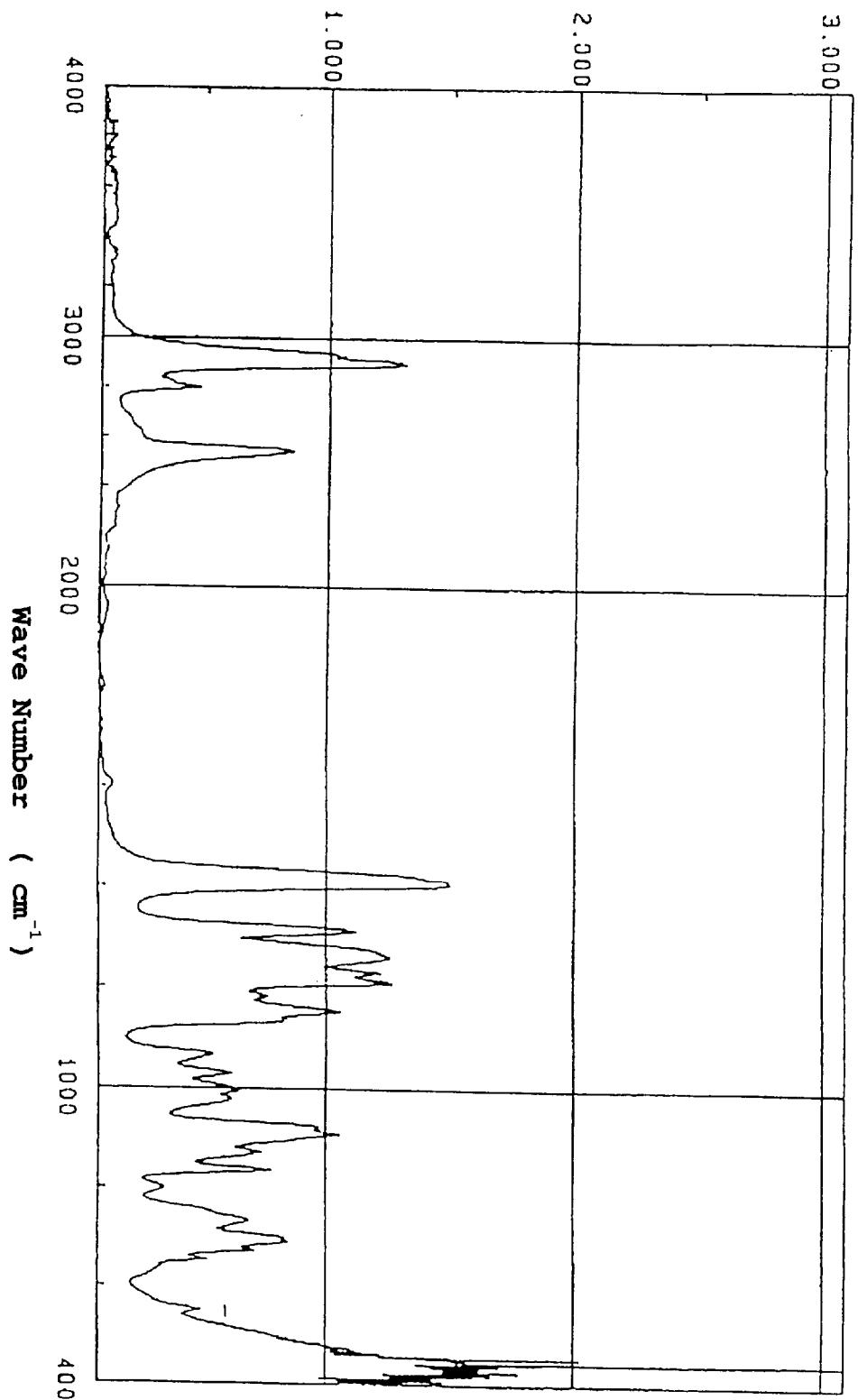
FIG. 2 is an IR spectrum of the oligomer produced in Example 1.

The NMR spectrum and IR spectrum are shown in FIGS. 1 and 2, respectively.

Specifically GPC analysis was conducted on a TOSOH column G200HXL with an RI detector, and with a flow rate of 0.8 ml/min at 40° C. The analysis showed 21.7% DMMD monomer, 26.4% DMMD dimer, 19.2% DMMD trimer, 13.6% DMMD tetramer, 8.7% DMMD pentamer and 10.0% DMMD hexamer and higher. Analysis of a second sample showed 21.9% monomer, 25.9% dimer, 19.9% trimer, 13.6% tetramer, 8.7% pentamer and 10% hexamer and above. It can generally be said that the distribution of the oligomer of the preferred embodiment is 21–22% monomer, 25–27% dimer, 19–20% trimer, 13–14% tetramer, 8–9% pentamer and 10–12% hexamer and above.

Examples 2 to 4

The same procedure as in Example 1 was repeated except that the catalyst and reaction conditions were changed as shown in Table 1. The resulting oligomer composed principally of monomers, dimers, and trimers of DMMD was found to have a refractive index and an Abbe's number as shown in Table 1. Table 1 shows that it is possible to selectively obtain with the process of the present invention a stable oligomer having a specific, predictable refractive index and Abbe's number if the reaction between DMMD and sulfur is carried out in a particular, predetermined molar ratio.

Example 5

The same procedure as in Example 1 was repeated except that the molar ratio of DMMD/S was changed to 3/2. The resulting oligomer was enriched in DMMD trimer and was found to have a refractive index and an Abbe's number as shown in Table 1.

TABLE 1

|  | Example No. | | | | |
| --- | --- | --- | --- | --- | --- |
|  | 1 | 2 | 3 | 4 | 5 |
| Raw material (mol) | | | | | |
| DMMD | 0.4 | 0.4 | 0.4 | 0.4 | 0.3 |
| S | 0.2 | 0.2 | 0.2 | 0.2 | 0.2 |
| Molar ratio of DMMD/s | 2/1 | 2/1 | 2/1 | 2/1 | 3/2 |
| Catalyst (mol %) | | | | | |
| DEA | 0.05 | | | | |
| TEA | | 0.05 | | | 0.05 |
| MPR | | | 0.05 | | |
| PPD | | | | 0.05 | |
| Largest portion of reaction product | Dimer | Dimer | Dimer | Dimer | Trimer |
| Yields (%) | 100 | 100 | 100 | 100 | 100 |
| Refractive index | 1.682 | 1.682 | 1.682 | 1.682 | 1.676* |
| Abbe's number | 34.7 | 34.7 | 34.6 | 34.7 | 34.2* |

*Measured at 70 ± 0.2° C.

Examples 6 to 12

The same procedure as in Example 1 was repeated except that the polythiol (as the starting material) and the catalyst were varied in type and amount as shown in Table 2. The resulting oligomers composed in largest part of dimers of polythiol found to have high refractive indexes and an Abbe's numbers as shown in Table 2.

TABLE 2

|  | Example No. | | | | | | |
| --- | --- | --- | --- | --- | --- | --- | --- |
|  | 6 | 7 | 8 | 9 | 10 | 11 | 12 |
| Raw material (mol) | | | | | | | |
| PETMA | 0.4 | | | | | | |
| PETMP | | 0.4 | | | | | |
| TMTG | | | 0.4 | | | | |
| m-XDT | | | | 0.4 | | | |
| DMP | | | | | 0.4 | | |
| DMDS | | | | | | 0.4 | |
| DMMP | | | | | | | 0.4 |
| S | 0.2 | 0.2 | 0.2 | 0.2 | 0.2 | 0.2 | 0.2 |
| Molar ratio of polythiol/S | 2/1 | 2/1 | 2/1 | 2/1 | 2/1 | 2/1 | 2/1 |

TABLE 2-continued

| | Example No. | | | | | | |
|---|---|---|---|---|---|---|---|
| | 6 | 7 | 8 | 9 | 10 | 11 | 12 |
| Catalyst (mol %) DEA | 0.05 | 0.05 | 0.05 | 0.05 | 0.05 | 0.05 | 0.05 |
| Largest portion of Reaction product | Dimer | Dimer | Dimer | Dimer | Dimer | Dimer | Dimer |
| Yields (%) | 100 | 100 | 100 | 100 | 100 | 100 | 100 |
| Refractive index | 1.572 | 1.545 | 1.545 | 1.664 | 1.643 | 1.613* | 1.654 |
| Abbe's number | 41.6 | 45.1 | 44.4 | 26.1 | 35.8 | 34.0* | 34.6 |

*Measured at 70 ± 0.2° C.

For reference, Table 3 shows the refractive indexes and Abbe's numbers of the thiols used as the starting material in Examples 1 to 12.

TABLE 3

| Compound | Refractive index | Abbe's number |
|---|---|---|
| DMMD | 1.646 | 35.2 |
| PETMA | 1.545 | 44.5 |
| PETMP | 1.532 | 45.8 |
| TMTG | 1.529 | 45.5 |
| m-XDT | 1.621 | 28.1 |
| DMP | 1.573 | 38.7 |
| DMDS | 1.594 | 35.6 |
| DMMP | 1.629 | 35.4 |

Abbreviations in Tables 1 to 3 denote the following compounds.
DMMD: 2,5-dimercaptomethyl-1,4-dithiane
PETMA: pentaerythritol tetramercaptoacetate
PETMP: pentaerythritol tetramercaptopropionate
TMTG: trimethylolpropane trimercaptoacetate
m-XDT: m-xylylene dithiol
DMP: 2,3-dimercapto-1-propanol
DMDS: 2-mercaptoethylsulfide
DMMP: 2,3-(dimercaptoethylthio)-1-mercaptopropane
DEA: diethylamine
TEA: triethylamine
MPR: morpholine
PPD: piperidine Tables 1 and 2 show that the process of the present invention permits the selective and stable production of polythiol oligomer with disulfide linkages, in large part dimers or trimers of polythiol having the functionality of two or above. It is also apparent from Tables 1 to 3 that the process of the present invention affords the polythiol oligomer which has a higher refractive index and an Abbe's number comparable to the starting thiol compound.

The present invention provides a process for reacting polythiol (having the functionality of two or above) with sulfur in a specific ratio in the presence of basic catalyst, thereby selectively, and consistently producing a polythiol oligomer with disulfide linkages. The resulting polythiol oligomer has a higher refractive index and Abbe's number comparable to the thiol starting material.

The thiol oligomer of the present invention described above, having a specific refractive index and Abbe's number (a low dispersive power), can be made, as described below, into an optical polymer which has a predictably high refractive index and a high Abbe's number (a low dispersive power). Because of these good optical properties, this optical polymer is widely applicable for use in optical materials and products such as lenses.

2. Optical Polymer made with Polythiol Oligomer of the Invention

In a further embodiment of the present invention there is provided a process for making an optical polymer, and the optical polymer thus produced.

A optical polymer according to the present invention is formed by copolymerizing a monomer mixture comprising:
(A) a polythiol group-containing component,
(B) a polyisocyanate group-containing component and/or,
(C) a polyfunctional vinyl group-containing component.

Component A

Component A includes the polythiol oligomer of the present invention represented by formula (I):

$$H \!\!-\!\!\left[\! S \diagup\!\!\diagdown\!\!\diagup\!\!\diagdown\!\!\diagup\!\! S \!-\! H \right]_n \tag{I}$$

(wherein n is an integer of up to 21.

Component A includes the polythiol oligomer of the invention described above (component a1) a disulfide-bond-free polythiol compound (component a2), and/or a disulfide-bond-containing polythiol oligomer compound (component a3).

The reasons that component a2 and/or component a3 are used together with component a1 in component A are as follows.

At least a part of the monomer component (A) is the necessary polythiol oligomer (component a1) produced according to the process described above. However, the polythiol oligomer of the present invention has quite a high viscosity. Therefore, for obtaining the desired optical polymer, it is not advisable that the viscosity of component A be higher than that of the polythiol oligomer. In order to control the viscosity of component A, a disulfide-bond-free polythiol compound having a relatively low viscosity (component a2) and/or a disulfide-bond-containing polythiol oligomer (component a3) other than the component a1 is used together with component a1. The viscosity can also be controlled by using low viscosity component B and/or low viscosity component C. Therefore, it is not indispensable in the present invention to use the component a2 and/or component a3 in component A.

The disulfide bond-free polythiol component a2 does not have a disulfide bond, and contains two or more mercapto groups (—SH). Component a2 may contain, other than the mercapto group, an active hydrogen-containing functional group such as an amino group or a hydroxyl group. Specific examples of component a2 include 2,5-dimercaptomethyl-1,4-dithian (DMMD), pentaerythritol tetrakismercaptoacetate, pentaerythritol tetrakismercaptopropionate, trimethylolpropane trismercaptoacetate, 2,3-dimercapto-1-propanol, 1,2-(dimercaptothio)-3-mercaptopropane, 1,2,3-trimercaptopropane, 2-mercaptoethyl sulfide, ethanedithiol, butanedithiol, hexanedithiol, benzenedithiol, benzenetrithiol, toluenedithiol and xylylenedithiol. Preferable are trimethylolpropane trismercaptoacetate, pentaerythritol tetrakismercaptopropionate and pentaerythritol tetrakismercaptoacetate (PETMA).

The mixing ratio of the polythiol oligomer component a1 of the present invention to the disulfide-bond-free polythiol component a2 is usually between 100:1 and 1:100, preferably between 100:1 and 1:1, most preferably between 100:1 and 2:1 (weight:weight). When the proportion of the disulfide-bond-free polythiol component a2 is too high, the properties of the polythiol oligomer (component a1) are reduced, making it difficult to form the desired optical polymer having a high refractive index and the high Abbe's number (low dispersion).

The disulfide bond-containing polythiol oligomer component a3 is a compound containing a disulfide bond and two or more mercapto groups (—SH). Component a3 may have a functional group other than the mercapto group, for example, an active hydrogen-containing functional group such as an amino group or a hydroxyl group.

Specific examples of component a3 include dimers or trimers which are bound through the disulfide bond, such as 2,3-dimercapto-1-propanol, 1,2-(dimercaptoethylthio)-3-mercaptopropane, 1,2,3-trimercaptopropane, 2-mercaptoethyl sulfide, benzenedithiol, benzenetriol, toluenedithiol, xylylenedithiol, ethanedithiol, butanedithiol and hexanedithiol.

Also available is a compound which is obtained by oligomerizing the above-mentioned disulfide bond-free polythiol compound by the method described hereinabove.

The mixing ratio of the polythiol oligomer (component a1) of the present invention to component a3 is usually between 100:1 and 1:100, preferably between 100:1 and 1:1, especially preferably between 100:1 and 2:1 (weight:weight). When the proportion of the disulfide bond-containing polythiol oligomer (component a3) is too high, the properties of the polythiol oligomer of the present invention are reduced, making it difficult to form the desired polymer for the optical material having the high refractive index and the high Abbe's number (low dispersion).

When component a2 and/or component a3 is used in combination with the component a1 in component A, the mixing ratio [a1/(a2+a3)] is usually between 100/1 and 1/1, preferably between 100/1 and 1/1, especially preferably between 100/1 and 2/1, (expressed in terms of a weight/weight).

Component B

Component B comprises a polyisocyanate group-containing compound, namely, a compound having at least two or more isocyanate groups (—NCO). The polyisocyanate group-containing compound may be a compound which can be used in the field of optical materials, and it is not particularly limited. However, since the viscosity of the monomer component A is relatively high, a polyisocyanate compound having a low viscosity is generally preferred. Specific examples of the isocyanate compounds which can be used in the present invention include hexamethylene diisocyanate, isophorone diisocyanate, bis(isocyanatomethyl)cyclohexane (HXDI), 1,3-diisocyanatocyclohexane (CHDI), 1,3,5-triisocyanatocyclohexane, dicyclohexylmethane diisocyanate, bis(isocyanatomethyl)bicyclopentane (NBDI), bis(isocyanatomethyl)bicycloheptane, benzene diisocyanate, toluene diisocyanate, xylylene diisocyanate, lysine ester triisocyanate, triisocyanatocyclohexane, tris(isocyanatomethyl)cyclohexane (HMTI), bicycloheptane triisocyanate, lysine ester triisocyanate (LyTI) and 2,5-diisocyanatomethyl-1,4-dithian. Preferable are bis(isocyanatomethyl)cyclohexane (HXDI), 1,3-diisocyanatocyclohexane (CHDI), 1,3,5-triisocyanatocyclohexane, bis(isocyanatomethyl)bicyclopentane (NBDI), tris(isocyanatomethyl)cyclohexane (HMTI) and 2,5-diisocyanatomethyl-1,4-dithian. Especially preferable are 1,3-diisocyanatocyclohexane (CHDI), 1,3,5-triisocyanatocyclohexane and 2,5-diisocyanato-1,4-dithian.

Component B may be composed of only one type of the above-mentioned polyisocyanate compounds or a mixture of two or more of these compounds.

Component C

The monomer component C comprises a polyfunctional vinyl group-containing compound, namely, a compound containing at least one vinyl group and/or a compound containing at least one vinyl group and at least one functional group other than a vinyl group. The polyfunctional vinyl group-containing compound may be any compound which is ordinarily used in the field of optical materials, and its type is not particularly limited. However, since the viscosity of the monomer component A is relatively high, a polyfunctional vinyl compound having a low viscosity is generally preferable. Specific examples of the polyfunctional vinyl compound which can be used in the present invention include 2,5-bis(2-thia-3-butenyl)-1,4-dithian (TBD), styrene, chlorostyrene, dibromostyrene, divinylbenzene, methyl (meth)acrylate, N-phenylmaleimide, N-cyclohexylmaleimide, phenyl (meth)acrylate, phenyl thio(meth)acrylate and di(meth)acrylphenyl sulfide. Preferable are 2,5-bis(2-thia-3-butenyl)-1,4-dithian (TBD) and divinylbenzene. Especially preferable is 2,5-bis(2-thia-3-butenyl)-1,4-dithian (TBD).

Component C may comprise only one type of the above-mentioned polyfunctional vinyl compounds or a mixture of two or more thereof.

The mixing ratio of the monomer components of the polymer for the optical material in the present invention is described hereinafter.

When the polymer for the optical material in the present invention comprises two components, namely, the polythiol group-containing compound as the monomer component A and the polyisocyanate group-containing compound as the monomer component B, the mixing ratio of the monomer component A to the monomer component B is usually between 1:2 and 2:1, preferably between 1:2 and 1:1, especially preferably between 1:1.2 and 1:1 in terms of a molar ratio of functional groups.

When the optical polymer of the present invention comprises a polythiol group-containing compound component A and a polyfunctional vinyl group-containing compound component C, the mixing ratio of component A to component C is usually between 1:1,000 and 1:1, preferably between 1:100 and 1:1, in terms of a molar ratio of functional groups.

When the optical polymer of the present invention comprises polythiol group-containing compound component A, polyisocyanate group-containing compound component B and polyfunctional vinyl group-containing compound component C, the mixing ratio of the monomer components A, B and C is usually between 1:10:1,000 and 10:0.01:1, preferably between 1:10:100 and 10:0.1:1, in terms of the molar ratio of functional groups.

The optical polymer of the present invention can contain, other than the above-mentioned monomer components A, B and C, an ultraviolet light absorber, an antioxidant, a dye and the like as required.

A process for producing the polymer for the optical material in the present invention is described below.

The polymer for the optical material in the present invention can be produced by forming a monomer mixture containing at least component A, component B and/or component C, and then subjecting this mixture to a known polymerization step such as heat polymerization, photopolymerization or the like in the presence of an appropriate amount of a polymerization catalyst. The conditions for the polymerization reaction are not particularly limited. The polymerization may be conducted under conditions which are ordinarily employed in the field of optical materials.

An optical product formed of the optical polymer of the present invention can be produced through cast polymerization, cutting-polishing, injection molding or the like. When the product is produced through cast polymerization, an internal mold release agent is used, as required.

The polymer for the optical material in the present invention has a high refractive index and a high Abbe's number (low dispersion), and the refractive index and the Abbe's number among product lots is constant. Accordingly, it can preferably be used as a material of optical products such as optical lenses, eyeglass lenses, prisms, optical fibers, substrates for recording information, color filters, infrared absorption filters and the like.

EXAMPLES

The optical polymer of the present invention is illustrated more specifically by referring to the following Examples and Comparative Examples. However, the present invention is not limited thereto.

The properties in the following Example and Examples were measured by the methods. Described above with respect to the polythiol olibomer examples.
Optical Resin Production Reference Example A polythiol oligomer, component A, was produced according to Example 1, above.

Example 13

A mixture containing 0.1 moles of the polythiol oligomer of Example 1, 0.1 moles of m-xylylene diisocyanate (XDI, monomer component B) and dimethyltin dichloride (DMTDC) in an amount corresponding to 0.05% by weight was fully stirred to form a uniform solution. This solution was then charged into two glass molds for forming a lens. The temperature was elevated to 50° C. over a period of 10 hours, then to 60° C. over a period of 5 hours, and further to 120° C. over a period of 2.5 hours. Finally, the reaction solution was heat-polymerized at 120° C. for 2.5 hours to give a colorless transparent polymer in the form of a lens. The properties of the resulting polymer are shown in Table 4.

Example 14

A mixture containing 0.1 moles of the polythiol oligomer of Example 1, 0.1 moles of 2,5-bis(2-thia-3-butenyl)-1,4-dithian (TBD, monomer component C) and azobisdimethylvaleronitrile (V-65) in an amount corresponding to 0.05% by weight was fully stirred to form a uniform solution. Subsequently, this solution was polymerized in the same manner as in Example 13 to give a polymer for a lens material. The properties of the resulting polymer are shown in Table 4.

Examples 15 to 18

The polymerization was conducted in the same manner as in Example 13 except that a polyisocyanate group-containing compound shown in Table 1 was used as the monomer component B to obtain a polymer for a lens material. The properties of the resulting polymer are shown in Table 4.

Examples 19 to 22

The polymerization was conducted in the same manner as in Example 13 except that a polyisocyanate group-containing compound shown in Table 4 was used as component B in an amount shown in Table 4 and a polyfunctional vinyl group-containing compound shown in Table 4 as component C in an amount shown in Table 4, respectively. The properties of the resulting polymer are shown in Table 4.

Examples 23 to 27

The polymerization was conducted in the same manner as in Example 13 except that the polythiol oligomer of Example 1 and 2,5-dimercaptomethyl-1,4-dithian (DMMD) were used as component A in amounts shown in Table 4, and the polyisocyanate compounds and polyfunctional vinyl group-containing compounds shown in Table 4 where used as components B and C in amounts shown to give a polymer for a lens material. The properties of the resulting polymer are shown in Table 4.

Comparative Example 1

A polymer which was formed by polymerizing 2,5-dimercaptomethyl-1,4-dithian (DMMD, monomer) and m-xylene diisocyanate (XDI) at a mixing ratio of 50:50 [Japanese Laid-Open Patent Application (Kokai) No. 236,386/1991, Example 1) exhibited a refractive index (nd) of 1.66 and an Abbe's number (Vd) of 32.

Comparative Example 2

A polymer which was formed by polymerizing 2,5-dimercaptomethyl-1,4-dithian (DMMD, monomer) and 1,3-bis(isocyanatomethyl)cyclohexane (HXDI) at a mixing ratio of 50:50 [Japanese Laid-Open Patent Application (Kokai) No. 236,386/1991, Example 8) exhibited a refractive index (nd) of 1.62 and an Abbe's number (Vd) of 38.

TABLE 4

| No. | Composition of monomer components | Mixing molar ratio | Refractive index/ Abbe's number (nd/Vd) | Heat resistance (Tg) (°C.) | Appearance |
| --- | --- | --- | --- | --- | --- |
| Ex. 13 | MDMS/XDI | 50/50 | 1.680/33 | 87 | colorless transparent |
| Ex. 14 | MDMS/TBD | 50/50 | 1.694/36 | — | colorless transparent |
| Ex. 15 | MDMS/CHDI | 50/50 | 1.660/36 | 88 | colorless transparent |
| Ex. 16 | MDMS/HMTI | 50/50 | 1.660/36 | 118 | colorless transparent |
| Ex. 17 | MDMS/NBDI | 50/50 | 1.651/37 | 91 | colorless transparent |
| Ex. 18 | MDMS/HXDI | 50/50 | 1.648/36 | 80 | colorless transparent |
| Ex. 19 | MDMS/XDI/TBD | 50/25/25 | 1.687/35 | — | colorless transparent |

TABLE 4-continued

| No. | Composition of monomer components | Mixing molar ratio | Refractive index/ Abbe's number (nd/Vd) | Heat resistance (Tg) (°C.) | Appearance |
|---|---|---|---|---|---|
| Ex. 20 | MDMS/HMTI/ TBD | 50/25/25 | 1.681/36 | 65 | colorless transparent |
| Ex. 21 | MDMS/XDI/ HMTI/TBD | 50/10/15/ 25 | 1.683/34 | 61 | colorless transparent |
| Ex. 22 | MDMS/XDI/ HMTI/TBD | 50/10/10/ 30 | 1.684/35 | 56 | colorless transparent |
| Ex. 23 | MDMS/DMMD/ HMTI/TBD | 16.5/33.5/ 35/15 | 1.660/37 | 90 | colorless transparent |
| Ex. 24 | MDMS/DMMD/ HMTI/TBD | 30/20/35/ 15 | 1.665/36 | 85 | colorless transparent |
| Ex. 25 | MDMS/DMMD/ HMTI/CHDI/ TBD | 25/25/ 22.5/20/ 7.5 | 1.670/36 | 67 | colorless transparent |
| Ex. 26 | MDMS/DMMD/ LyTI | 25/25/50 | 1.645/37 | 100 | colorless transparent |
| Ex. 27 | MDMS/DMMD/ HXDI/HMTI/ TBD | 20/30/10/ 32.5/7.5 | 1.650/37 | 115 | colorless transparent |
| C. Ex. 1 | DMMD/XDI | 50/50 | 1.66/32 | 97 | colorless transparent |
| C. Ex. 2 | DMMD/HXDI | 50/50 | 1.62/38 | 108 | colorless transparent |

Ex. . . . Example
C. Ex. . . . Comparative Example

The abbreviations in Table 4 refer to the following compounds.

MDMS: (4-mercaptomethyl-2,5-dithianyl)methyl disulfide [oligomer composed mainly of the dithiol compound (I)]

CHDI: 1,3-diisocyanatocyclohexane

HMTI: tris(isocyanatomethyl)cyclohexane

NBDI: bis(isocyanatomethyl)bicyclopentane

HXDI: 1,3-bis(isocyanatomethyl)cyclohexane

TBD: 2,5-bis(2-thia-3-butenyl)-1,4-dithian

DMMD: 2,5-dimercaptomethyl-1,4-dithian

LyTI: lysine ester triisocyanate

From the results in Table 4, it is clear that the polymers obtained in Examples 13 to 27 exhibit quite a high refractive index (nd) of from 1.645 to 1.694 and a high Abbe's number (Vd, low dispersion) of from 33.0 to 37 and both of the properties are improved at the same time. Meanwhile, in Comparative Example 1, the refractive index is relatively high, but the Abbe's number is as low as 32. Further, in Comparative Example 2, the Abbe's number is as high as 38, but the refractive index is low.

As stated above, the present invention can provide an optical polymer for an optical material of which the refractive index and the Abbe's number (dispersion) are improved at the same time by copolymerizing an oligomer composed mainly of a dithiol compound (I) having a high refractive index and a high Abbe's number (low dispersion) as a polythiol group-containing compound and copolymerizing the same with a polyisocyanate group-containing compound and/or a polyfunctional vinyl group-containing compound.

In accordance with the present invention, a polymer for an optical material can be provided which has a stable high refractive index and a stable high Abbe's number (low dispersion) and which is not influenced by the change in the reaction conditions, unlike a copolymer obtained upon using an oligomer mixture of DMMD disclosed in Japanese Laid-Open Patent Application (Kokai) No. 118,390/1995 as a polythiol group-containing compound. Further, an optical product having excellent optical properties can industrially be provided.

While the present invention has been described in terms of various preferred embodiments, one of ordinary skill in the art will recognize that modifications, substitutions and improvements can be made while remaining within the scope and spirit of the present invention. The scope of the invention is determined solely by the appended claims.

What is claimed is:

1. A process for producing a polythiol oligomer, comprising reacting a polythiol (having a functionality of at least two) with sulfur in a molar ratio of m to (m−1) (where m is an integer of 2 to 21) in the presence of a basic catalyst such that the degree of oligomerization is m (where m is defined as above) under conditions sufficient to produce a polythiol oligomer having disulfide linkages.

2. A process as defined in claim 1, wherein m is an integer of 2, 3, or 4.

3. A process as defined in claim 1, comprising reacting polythiol with sulfur in a molar ratio of 2:1, thereby producing a polythiol oligomer comprising in largest part dimer.

4. A process as defined in claim 1, wherein said polythiol is selected from the group consisting of pentaerythritol tetramercaptoacetate, pentaerythritol tetramercaptopropionate, trimethylolpropane trimercaptoacetate, m-xylylenedithiol, 2,3-dimercapto-1-propanol, 2-mercaptoethylsulfide, and 2,3-(dimercaptoethylthio)-1-mercaptopropane.

5. A process as defined in claim 1, wherein said basic catalyst is ammonia or amine.

6. A process as defined in claim 5, wherein said amine is selected from the group consisting of diethylamine, triethylamine, n-butylamine, morpholine, and iperidine or a combination of members of the group.

7. A process comprising 2,5-dimercaptomethyl-1,4-dithiane (DMMD) with sulfur in a molar ratio 2:1 or 3:2 in the presence of a basic catalyst under conditions sufficient to cause a reaction to take place, thereby producing a polythiol oligomer.

8. A process according to claim 7, wherein said polythiol oligomer has a structure of the following formula:

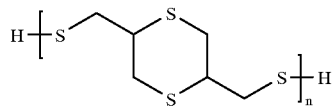

(wherein n is an integer of 2 to 21).

9. A process according to claim 8, wherein n is in largest part 2.

10. A process according to claim 8, wherein n is in largest part 3.

11. A polythiol oligomer produced by the process of any one of claims 1–10.

12. An optical polymer formed by reacting a mixture comprising the following components (A), (B) and (C) under conditions sufficient for copolymerization to take place:
   (A) a polythiol group-containing component, including a polythiol oligomer (component a1) made by reacting 2,5-dimercaptomethyl-1,4-dithiane (DMMD) with sulfur in a molar ratio 2:1 or 3:2 in the presence of a basic catalyst
   (B) a polyisocyanate group-containing component, and/or
   (C) a polyfunctional vinyl group-containing component.

13. A polymer according to claim 11, wherein said component a1 is a polythiol oligomer of the following formula (I):

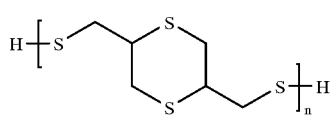

(wherein n is an integer of from 2 to 21).

14. A polymer according to claim 12, wherein said component (A) further comprises a disulfide bond-free polythiol component a2.

15. A polymer according to claim 12, wherein said component (A) further comprises a disulfide-bond-containing component a3.

16. A polymer according to claim 14, wherein said component (A) further comprises a disulfide-bond-containing component a3.

17. A polymer according to claim 14, wherein said component a2 comprises at least one member of the group consisting of 2,5-dimercaptomethyl-1,4-dithian, pentaerythritol tetrakismercaptoacetate, pentaerythritol tetrakismercaptopropionate, trimethylolpropane trismercaptoacetate, 2,3-dimercapto-1-propanol, 1,2-(dimercaptoethylthio)-3-mercaptopropane, 1,2,3-trimercaptopropane, 2-mercaptoethyl sulfide, benzenedithiol, benzenetrithiol, toluenedithiol and xylylenedithiol.

18. A polymer according to claim 16, wherein said component a2 comprises at least one member of the group consisting of 2,5-dimercaptomethyl-1,4-dithian, pentaerythritol tetrakismercaptoacetate, pentaerythritol tetrakismercaptopropionate, trimethylolpropane trismercaptoacetate, 2,3-dimercapto-1-propanol, 1,2-(dimercaptoethylthio)-3-mercaptopropane, 1,2,3-trimercaptopropane, 2-mercaptoethyl sulfide, benzenedithiol, benzenetrithiol, toluenedithiol and xylylenedithiol.

19. A polymer according to claim 15, wherein said component a3 is selected from the group consisting of oligomers formed from one or more of 2,3-dimercapto-1-propanol, 1,2-(dimercaptoethylthio)-3-mercaptopropane, 2-mercaptoethyl sulfide, benzenedithiol, benzenetrithiol, toluenedithiol, xylylenedithiol, ethanedithiol, butanedithiol and hexanedithiol.

20. A polymer according to claim 16, wherein said component a3 is selected from the group consisting of oligomers formed from one or more of 2,3-dimercapto-1propanol, 1,2-(dimercaptoethylthio)-3-mercaptopropane, 2-mercaptoethyl sulfide, benzenedithiol, benzenetrithiol, toluenedithiol, xylylenedithiol, ethanedithiol, butanedithiol and hexanedithiol.

21. A polymer according to claim 12, wherein said component B comprises at least one member selected from the group consisting of 2,5-diisocyanatomethyl-1,4-dithian, 1,3-diisocyanatocyclohexane (CHDI), 1,3,5-triisocyanatocyclohexane, tris(isocyanatomethyl) cyclohexane (HMTI), bis(isocyanatomethyl)bicyclopentane (NBDI) and 1,3-bis(isocyanatomethyl)cyclohexane (HXDI).

22. A polymer according to claim 12, wherein component B comprises at least one of 2,5-diisocyanatomethyl-1,4-dithian, and 1,3-diisocyanatocyclohexane (CHDI).

23. A polymer according to claim 12, wherein component C comprises 2,5-bis(2-thia-3-butenyl)-1,4-dithian (TBD).

24. The polymer according to claim 12, obtained by copolymerizing components A and B in a ratio of A to B in the range of from 1:2 to 2:1 expressed in molar ratio of functional groups.

25. The polymer according to claim 12, obtained by copolymerizing components A and C in a ratio of A to C in the range of from 1:1,000 to 1:1 expressed in molar ratio of functional groups.

26. The polymer according to claim 12, obtained by copolymerizing components A, B and C in a ratio of A:B:C in the range of from 1:10:1,000 to 10:0.01:1 expressed in molar ratio of functional groups.

27. A lens comprising the optical polymer of any one of claims 12–26.

* * * * *